United States Patent [19]

Petersen et al.

[11] Patent Number: 4,599,334
[45] Date of Patent: Jul. 8, 1986

[54] 7-(3-ARYL-1-PIPERAZINYL)- AND 7-(3-CYCLOHEXYL-1-PIPERAZINYL)-3-QUINOLONECARBOXYLIC ACID ANTIBACTERIALS

[75] Inventors: Uwe Petersen; Klaus Grohe, both of Leverkusen; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 735,493

[22] Filed: May 17, 1985

[30] Foreign Application Priority Data

Jun. 4, 1984 [DE] Fed. Rep. of Germany ....... 3420798

[51] Int. Cl.$^4$ .................. A61K 31/495; C07D 401/04
[52] U.S. Cl. .................................... 514/253; 544/363; 546/156
[58] Field of Search .......................... 544/363; 514/253

[56] References Cited

U.S. PATENT DOCUMENTS 4,398,029 8/1983 Irikura et al. ........................ 544/363
4,544,658 10/1985 Petersen et al. ..................... 544/363

FOREIGN PATENT DOCUMENTS 0049355 8/1981 European Pat. Off. .
0113093 7/1984 European Pat. Off. .
0126355 11/1984 European Pat. Off. .
3306772 8/1984 Fed. Rep. of Germany ...... 544/363
0010580 1/1984 Japan .................................. 544/363

OTHER PUBLICATIONS

Hokuriku Pharm K.K. 84-052418/09, Hokr 08/07/82-J 5 9010-580A.
Hokuriku Pharm K.K. 84-078414/13, Hokr 11/08/82-J 5 9029-685A.

Primary Examiner—Glennon H. Hollrah
Assistant Examiner—James H. Turnipseed
Attorney, Agent, or Firm—Sprung Horn Kramer & Woods

[57] ABSTRACT

Novel 1-cyclopropyl-4-fluoro-1,4-dihydro-4-oxo-7-(1-piperazinyl)-3-quinolinecarboxylic acid antibacterials of the formula

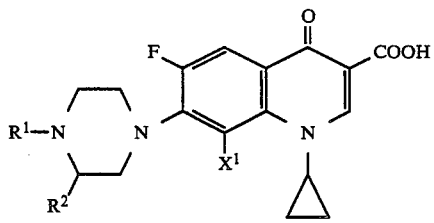

in which $R^1$ is hydrogen, alkyl with 1 to 4 carbon atoms and optionally substituted by hydroxyl, methoxy, amino, dimethylamino, halogen, cyano or alkoxycarbonyl having 1 or 2 carbon atoms in the alkyl moiety, or is oxoalkyl having up to 4 carbon atoms, phenacyl, or acyl having 1 to 4 carbon atoms, phenacyl, or acyl having 1 to 4 carbon atoms, $R^2$ is phenyl or cyclohexyl optionally substituted up to three times by halogen, methyl, phenyl, cyano, hydroxyl, methoxy, benzyloxy, amino, methylamino, dimethylamino, piperidino or nitro, or is methylenedioxyphenyl, methylenedioxycyclohexyl, furyl, tetrahydrofuryl or thienyl, and $X^1$ is hydrogen or fluorine, or pharmaceutically ultizable hydrates, acid addition salts, alkali metal salts or alkaline earth metal salts thereof.

12 Claims, No Drawings

7-(3-ARYL-1-PIPERAZINYL)- AND 7-(3-CYCLOHEXYL-1-PIPERAZINYL)-3-QUINOLONECARBOXYLIC ACID ANTIBACTERIALS

The present invention relates to new 1-cyclopropyl-1,4-dihydro-4-oxo-3-quinolinecarboxylic acids, process for their preparation and antibacterial agents and feed additives containing them.

It has been found that the new 1-cyclopropyl-6-fluoro-1,4-dihydro-4-oxo-7-(1-piperazinyl)-3-quinolinecarboxylic acids of the formula (I)

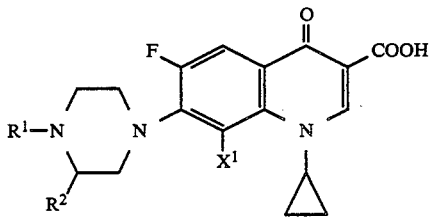

in which $R^1$ denotes hydrogen, straight-chain or branched alkyl which has 1 to 4 carbon atoms and is optionally substituted by hydroxyl, methoxy, amino, dimethylamino, halogen, such as, for example, fluorine or chlorine, cyano or alkoxycarbonyl having 1 or 2 carbon atoms in the alkyl moiety, oxoalkyl having up to 4 carbon atoms, phenacyl, or acyl having 1 to 4 carbon atoms, $R^2$ denotes phenyl and cyclohexyl which are optionally singly to triply substituted by halogen, such as, for example, chlorine, bromine or fluorine, methyl, phenyl, cyano, hydroxyl, methoxy, benzyloxy, amino, methylamino, dimethylamino, piperidino or nitro, methylenedioxyphenyl, methylenedioxycyclohexyl, furyl, tetrahydrofuryl or thienyl, and $X^1$ denotes hydrogen or fluorine, and their pharmaceutically utilizable hydrates, acid addition salts, alkali metal and alkaline earth metal salts Foreign countries have high antibacterial activity.

Preferred compounds of the formula (I) are those in which $R^1$ denotes hydrogen, straight-chain or branched alkyl which has 1 to 4 carbon atoms and is optionally substituted by hydroxyl, methoxy, halogen, such as, for example, fluorine or chlorine, cyano or alkoxycarbonyl having 1 or 2 carbon atoms in the alkyl moiety, oxoalkyl having up to 4 carbon atoms, phenacyl, formyl or acetyl, $R^2$ denotes phenyl and cyclohexyl which are optionally singly to triply substituted by chlorine, bromine, fluorine, methyl, phenyl, cyano, hydroxyl, methoxy, benzyloxy, amino, piperidino or nitro, and thienyl, and $X^1$ denotes hydrogen or fluorine.

Particularly preferred compounds of the formula (I) are those in which $R^1$ denotes hydrogen, straight-chain or branched alkyl which has 1 to 3 carbon atoms and is optionally substituted by hydroxyl, methoxy, cyano or alkoxy carbonyl having 1 or 2 carbon atoms in the alkyl moiety, oxoalkyl having up to 4 carbon atoms, phenacyl, formyl or acetyl, $R^2$ denotes phenyl and cyclohexyl which are optionally singly to triply substituted by chlorine, bromine, fluorine, methyl, phenyl, hydroxyl, methoxy, benzyloxy, amino, piperidino or nitro, and thienyl, and $X^1$ denotes hydrogen or fluorine.

It has also been found that the compounds of the formula (I) are obtained when 1-cyclopropyl-7-fluoro-1,4-dihydro-4-oxo-3-quinolinecarboxylic acids of the formula (II)

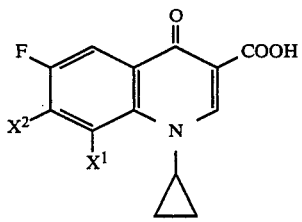

in which $X^1$ has the abovementioned meaning, and $X^2$ represents halogen, in particular fluorine or chlorine, are reacted with piperazines of the formula (III)

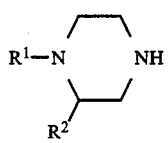

in which $R^1$ and $R^2$ have the abovementioned meaning, where appropriate in the presence of acid-binding agents (method A).

The compounds according to the invention, of the formula (I), can also be obtained by reacting a 7-(1-piperazinyl)-3-quinolonecarboxylic acid of the formula (IV)

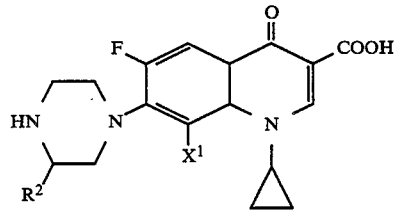

in which $R^2$ and $X^1$ have the abovementioned meaning, with compounds of the formula (V)

    (V)

in which $R^1$ has the abovementioned meaning but cannot be hydrogen, and

X denotes fluorine, bromine, iodine, hydroxyl, acyloxy, phenoxy or 4-nitrophenoxy, where appropriate in the presence of acid-binding agents (method B).

The compounds according to the invention, of the formula (I), are also obtained when a 7-(1-piperazinyl)-3-quinolonecarboxylic acid of the formula (IV) is reacted with a Michael-acceptor of the formula (VI)

    (VI)

in which $R^3$ represents CN, $CH_3CO$ or $COOR^4$, $R^4$ denoting methyl or ethyl (method C).

If, in the reaction by method A, 2-phenylpiperazine and 1-cyclopropyl-6,7,8-trifluoro-1,4-dihydro-4-oxo-3-quinolinecarboxylic acid are used as the starting materials, then the course of the reaction can be represented by the following equation:

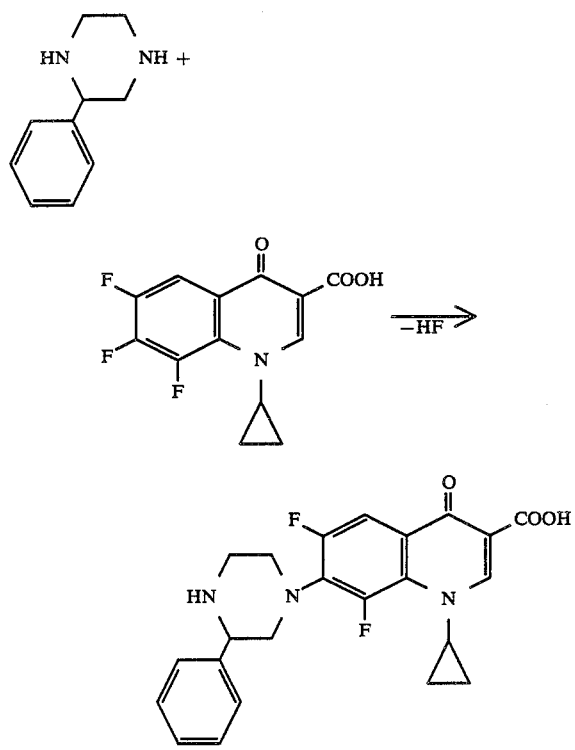

If, in the reaction by method B, ethyl iodide and 1-cyclopropyl-6,8-difluoro-1,4-dihydro-4-oxo-7-(3-phenyl-1-piperazinyl)-3-quinolinecarboxylic acid are used as the starting materials, then the course of the reaction can be represented by the following equation:

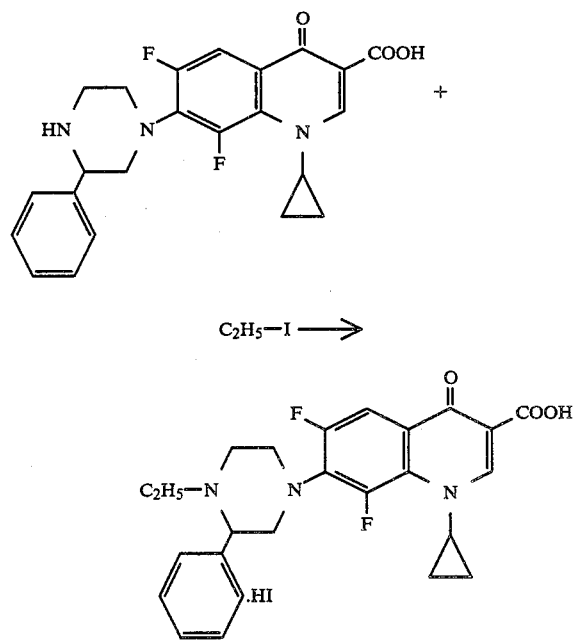

If, in the reaction by method C, for example 1-cyclopropyl-6-fluoro-1,4-dihydro-4-oxo-7-(3-phenyl-1-piperazinyl)-3-quinolinecarboxylic acid and methyl vinyl ketone are used as the starting compounds, then the course of the reaction can be represented by the equation below:

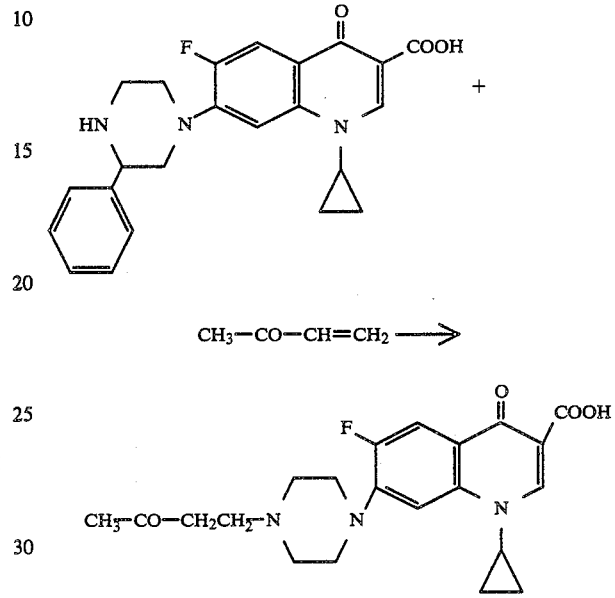

Some of the quinolonecarboxylic acids (II) used as starting compounds are known (see DE-OS (German Published Specification) No. 3,142,854: 7-chloro-1-cyclopropyl-6-fluoro-1,4-dihydro-4-oxo-3-quinolinecarboxylic acid), or they can be prepared by the following route:

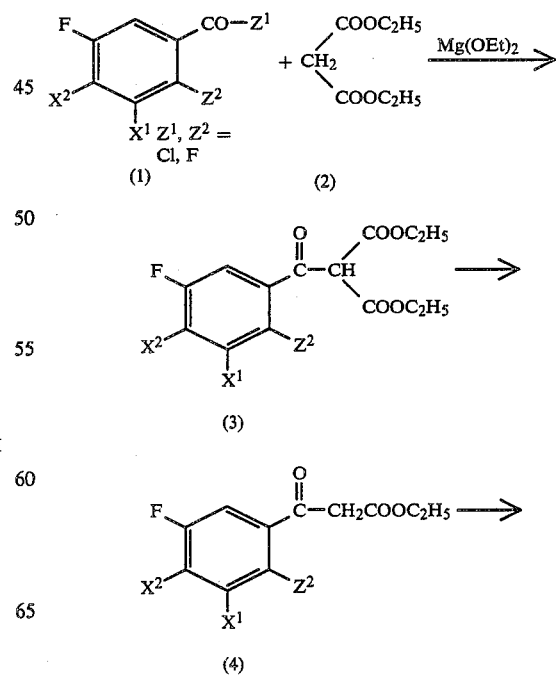

-continued

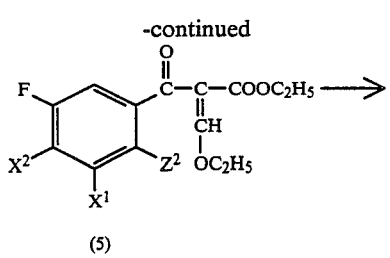

(5)

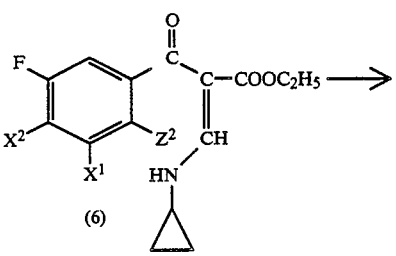

(6)

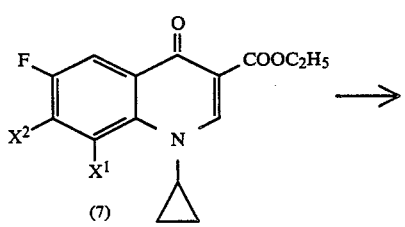

(7)

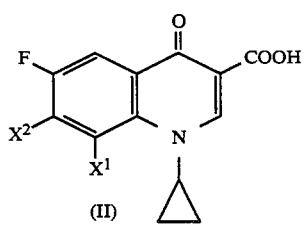

(II)

According to this, diethyl malonate (2) is acylated with the appropriate benzoyl fluoride or chloride (1) in the presence of magnesium ethylate to give the aroylmalonate (3) (Organicum, 3rd edition, 1964 page 438).

By partial hydrolysis and decarboxylation of (3) in aqueous medium with catalytic amounts of sulphuric acid or p-toluenesulphonic acid, the ethyl aroylacetate (4) is obtained in good yield, and this is converted into the corresponding ethyl 2-benzoyl-3-ethoxyacrylate (5) using triethyl orthoformate/acetic anhydride. The reaction of (5) with cyclopropylamine in a solvent, such as, for example, methylene chloride, alcohol, chloroform, cyclohexane or toluene leads, in a slightly exothermic reaction, to the desired intermediate (6).

The cyclization reaction (6)→(7) is carried out in a temperature range from about 60° to 300° C., preferably 80° to 180° C.

The diluents which can be used are dioxane, dimethyl sulphoxide, N-methylpyrrolidone, sulpholane, hexamethylphosphoric triamide and, preferably, N,N-dimethylformamide.

Suitable acid-binding agents for this reaction step are potassium tert.-butanolate, butyllithium, lithiumphenyl, phenyl magnesium bromide, sodium methylate, sodium hydride sodium or potassium carbonate. When the intention is to eliminate hydrogen fluoride ($Z^2$=F), potassium or sodium fluoride has also proved to be particularly suitable. It may be advantageous to use an excess of 10 mol-% of base.

The ester hydrolysis of (7) under basic or acid conditions, which is carried out in the last step, leads to the appropriate cyclopropyl-6-fluoro-1,4-dihydro-4-oxo-3-quinolinecarboxylic acid (II).

The 2,3,4,5-tetrafluorobenzoyl chloride (1) ($X^1=X^2=Z^2$=F, $Z^1$=Cl), which is used as starting material for this synthetic route, was obtained from 2,3,4,5-tetrafluorobenzoic acid which is known from the literature (G. G. Yakobson, V. N. Odinokov and N. N. Vorozhtsov Jr., Zh. Obsh. Khim. 36, 139 (1966)) using thionyl chloride in the customary manner. It has a boiling point of 75°-80° C./17 mbar. 2,3,4,5-tetrafluorobenzoyl fluoride has a boiling point of 46° to 47° C./20 mbar ($n_d^{20}$: 1.4375).

2,4,5-trifluorobenzoyl fluoride (1) ($X^1$=H, $X^2=Z^1=Z^2$=F) which is used as a starting material was prepared analogously from 2,4,5-trifluorobenzoic acid which is known from the literature (I. J. DeGraw, M. Corey and W. A. Skinner, J. Chem. Eng. Data 13, 587 (1968)). It has a boiling point of 53°-56°/18 mbar ($n_D^{20}$: 1.4546).

The 2-substituted piperazines (III) which are used as starting materials are known or can be obtained from processes known from the literature (for example: U.S. Pat. No. 4,166,180; J. Med. Chem. 26, 1116 (1983)). The following may be mentioned as examples:

2-phenylpiperazine, 2-(4-chlorophenyl)piperazine, 2-(4-fluorophenyl)piperazine, 2-(4-bromophenyl)piperazine, 2-(4-methylphenyl)piperazine, 2-(4-biphenylyl)piperazine, 2-(4-methoxyphenyl)piperazine, 2-(4-benzyloxyphenyl)piperazine, 2-(4-hydroxyphenyl)piperazine, 2-(3-hydroxyphenyl)piperazine, 2-(2-hydroxyphenyl)piperazine, 2-(4-nitrophenyl)piperazine, 2-(3-nitrophenyl)piperazine, 2-(4-aminophenyl)piperazine, 2-(4-piperidinophenyl)piperazine, 2-(3,4-dimethoxyphenyl)piperazine, 2-(3,4,5-trimethoxyphenyl)piperazine, 2-(3,4-dimethoxy-6-methyl)piperazine, 2-(3,4-methylenedioxyphenyl)piperazine, 2-(4-cyanophenyl)piperazine, 2-(2-thienyl)piperazine or 2-(2-furyl)piperazine. In accordance with German Appln. No. P 34 20 782.1, filed June 4, 1984, (Le,A 23 097), 2-cyclohexypiperazines are obtained by catalytic hydrogenation of corresponding 2-arylpiperazines; for example 2-cyclohexylpiperazine (melting point 82°-83° C.).

The compounds of the formula (V) which are used as starting materials are known. The following may be mentioned as examples:

methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.butyl chloride, formic acid, formic acidic anhydride, acetic anhydride or acetyl chloride.

The compounds of the formula (VI) which can be used according to the invention are known. The following may be mentioned as examples:

acrylonitrile, methyl vinyl ketone, methyl acrylate and ethyl acrylate.

The reaction of (II) with (III) by method A is preferably carried out in a diluent such as dimethyl sulphoxide, N,N-dimethylformamide, hexamethylphosphoric trisamide, sulpholane, water, an alcohol, such as methanol, ethanol, n-propanol, isopropanol or glycol monomethyl ether, or pyridine. It is likewise possible to use mixtures of these diluents.

All customary inorganic and organic acid-binding agents can be used as the acid-binding agent. These preferably include the alkali metal hydroxides, alkaline metal carbonates, organic amines and amidines. The following may be specifically mentioned as particularly suitable: triethylamine, 1,4-diazabicyclo[2.2.2]octane (DABCO), excess amine (III) or 1,8-diazabicyclo[5.4.0]undec-7-ene (DBU).

The reaction temperatures can be varied within a wide range. In general, the reaction is carried out between about 20° and 200° C., preferably between 80° and 180° C.

The reaction can be carried out under atmospheric pressure but also under elevated pressure. In general, it is carried out under pressures between about 1 and about 100 bar, preferably between 1 and 10 bar.

When carrying out the process according to the invention, 1 to 5 moles, preferably 1 to 3 moles, of the piperazine (III) are used for 1 mole of the carboxylic acid (II).

The reaction of (IV) with (V) is preferably carried out in a diluent such as dimethyl sulphoxide, dioxane, N,N-dimethylformamide, hexamethylphosphoric trisamide, sulpholane, water, an alcohol, such as methanol, ethanol, n-propanol, isopropanol, glycol monomethyl ether or pyridine. It is likewise possible to use mixtures of these diluents.

All customary inorganic and organic acid-binding agents can be used as the acid-binding agent. These preferably include the alkaline metal hydroxides, alkaline metal carbonates, organic amines and amidines. The following may be specifically mentioned as particularly suitable: triethylamine, 1,4-diazabicyclo[2.2.2]octane (DABCO) or 1,8-diazabicyclo[5.4.0]undec-7-ene (DBU).

The reaction temperatures can be varied within a wide range. In general, the reaction is carried out between about 20° and about 180° C., preferably between 40° and 110° C.

The reaction can be carried out under atmospheric pressure but also under elevated pressure. In general, it is carried out under pressures between about 1 and about 100 bar, preferably between 1 and 10 bar.

When carrying out the process according to the invention by method B, 1 to 4 moles, preferably 1 to 1.5 mole, of the compound (V) are used for 1 mole of compound (IV).

The reaction of (I) with (VI) (method C) is carried out in a diluent such as N,N-dimethylformamide, dioxane, tetrahydrofuran, pyridine, water or in mixtures of these diluents. The reaction temperatures can be varied within a wide range. In general, the reaction is carried out between about 0° C. and about 140° C., preferably between 10° and 100° C.

The reaction can be carried out under atmospheric pressure but also under elevated pressure. In general, it is carried out under pressures between about 1 and about 100 bar, preferably between 1 and 10 bar.

When carrying out the process according to the invention, 1 to 5 moles, preferably 1 to 2 moles, of compound (VI) are used for 1 mole of compound (I).

Apart from the compounds detailed in the examples, the following may be specifically mentioned as new active compounds, 1-cyclopropyl-6-fluoro-1,4-dihydro-7-(4-methyl-3-phenyl-1-piperazinyl)-4-oxo-3-quinolinecarboxylic acid, 7-(4-butyl-3-phenyl-1-piperazinyl)-1-cyclopropyl-6-fluoro-1,4-dihydro-4-oxo-3-quinolinecarboxylic acid, 1-cyclopropyl-6-fluoro-1,4-dihydro-7-[4-(2-hydroxyethyl)-3-phenyl-1-piperazinyl]-4-oxo-3-quinolinecarboxylic acid, 1-cyclopropyl-6-fluoro-1,4-dihydro-7-[4-(2-methoxyethyl)-3-phenyl-1-piperazinyl]-4-oxo-3-quinolinecarboxylic acid, 7-[4-(2-aminoethyl)-3-phenyl-1-piperazinyl]-1-cyclopropyl-6-fluoro-1,4-dihydro-4-oxo-3-quinolinecarboxylic acid, 1-cyclopropyl-6-fluoro-1,4-dihydro-7-[4-(2-dimethylaminoethyl)-3-phenyl-1-piperazinyl]-4-oxo-3-quinolinecarboxylic acid, 1-cyclopropyl-6-fluoro-7-[4-(2-fluoroethyl)-3-phenyl-1-piperazinyl]-1,4-dihydro-4-oxo-3-quinolinecarboxylic acid, 7-[4-(2-cyanoethyl)-3-phenyl-1-piperazinyl]-1-cyclopropyl-6-fluoro-1,4-dihydro-4-oxo-3-quinolinecarboxylic acid, 1-cyclopropyl-6-fluoro-1,4-dihydro-7-[4-(2-methoxycarbonylethyl)-3-phenyl-1-piperazinyl]-4-oxo-3-quinolinecarboxylic acid, 1-cyclopropyl-6-fluoro-1,4-dihydro-4-oxo-7-(4-phenacyl-3-phenyl-1-piperazinyl)-3-quinolinecarboxylic acid, 1-cyclopropyl-6-fluoro-7-(4-formyl-3-phenyl-1-piperazinyl)-1,4-dihydro-4-oxo-3-quinolineocarboxylic acid, 7-(4-acetyl-3-phenyl-1-piperazinyl)-1-cyclopropyl-6-fluoro-1,4-dihydro-4-oxo-3-quinolinecarboxylic acid, 1-cyclopropyl-6-fluoro-1,4-dihydro-7-[3-(4-methylcyclohexyl)-1-piperazinyl]-4-oxo-3-quinolinecarboxylic acid, 1-cyclopropyl-6-fluoro-1,4-dihydro-7-[3-(3,4,5-trimethoxyphenyl)-1-piperazinyl]-4-oxo-3-quinolinecarboxylic acid, 1-cyclopropyl-6-fluoro-1,4-dihydro-7-[3-(3,4-methylenedioxyphenyl)-1-piperazinyl]-4-oxo-3-quinolinecarboxylic acid, 7-[3-(4-cyanophenyl)-1-piperazinyl]-1-cyclopropyl-6-fluoro-1,4-dihydro-4-oxo-3-quinolinecarboxylic acid, 7-[3-(3-aminophenyl)-1-piperazinyl]-1-cyclopropyl-6-fluoro-1,4-dihydro-4-oxo-3-quinolinecarboxylic acid, 1-cyclopropyl-6-fluoro-7-[3-(2-furyl)-1-piperazinyl]-1,4-dihydro-4-oxo-3-quinolinecarboxylic acid, 1-cyclopropyl-6-fluoro-1,4-dihydro-7-[3-(2-tetrahydrofuryl)-1-piperazinyl]-4-oxo-3-quinolinecarboxylic acid, 1-cyclopropyl-6-fluoro-1,4-dihydro-7-[3-(4-hydroxycyclohexyl)-1-piperazinyl]-4-oxo-3-quinolinecarboxylic acid, 7-[3-(3-aminocyclohexyl)-1-piperazinyl]-1-cyclopropyl-6-fluoro-1,4-dihydro-4-oxo-3-quinolinecarboxylic acid, 1-cyclopropyl-7-(4-ethyl-3-phenyl-1-piperazinyl)-6,8-difluoro-1,4-dihydro-4-oxo-3-quinolinecarboxylic acid, 1-cyclopropyl-6,8-difluoro-7-[3-(4-fluorophenyl)-4-(3-oxobutyl)-1-piperazinyl-1,4-dihydro-4-oxo-3-quinolinecarboxylic acid, and 1-cyclopropyl-6,8-difluoro-7-[4-formyl-3-(2-thienyl)-1-piperazinyl]-1,4-dihydro-4-oxo-3-quinolinecarboxylic acid.

The compounds according to the invention are of low toxicity and exhibit a broad antibacterial spectrum toward Gram-positive and Gram-negative organisms, in particular toward Enterobacteriaceae, especially including those which are resistant to various antibiotics, such as, for example, penicillins, cephalosporins, aminoglycosides, sulphonamides and tetracyolines.

These valuable properties make it possible to use them as chemotherapeutic active compounds in medicine and as substances for the preservation of inorganic and organic materials, especially of organic materials of every type, for example polymers, lubricants, dyes, fibers, leather, paper and wood, of foodstuffs and of water.

The compounds according to the invention are active against a very broad spectrum of microorganisms. It is possible with their aid to combat Gram-negative and Gram-positive bacteria and bacteroid microorganisms, and to prevent, ameliorate and/or cure illnesses caused by these pathogens.

The compounds according to the invention are particularly active against bacteria and bacteroid microorganisms. Thus they are particularly well suited for the prophylaxis and chemotherapy of local and systemic infections which are caused by these pathogens in human and veterinary medicine.

For example, local and/or systemic illnesses which are caused by the following pathogens or by mixtures of the following pathogens can be treated and/or prevented: Micrococcaceae, such as Staphylococci, for example *Staph. aureus, Staph. epidermidis* (Staph.=Staphylococcus); Lactobacteriaceae, such as Streptococci, for example *Streptococcus pyogenes*, α- and β-haemolytic Streptococci, non-σ-haemolytic Streptococci, Enterococci and *Diplococcus pneumoniae* (Pneumococci), Enterobacteriaceae, such as Escherichiae-bacteria of the Coli group: Escherichia-bacteria, for example *Escherichia coli*, Enterobacter bacteria, for example *E. aerogenes, E. cloacae*, (E.=Enterobacter), Klebsiella bacteria, for example *K. pneumoniae* (K.=Klebsiella), Serratia, for example *Serratia marcescens*, Proteae bacteria of the proteus group: Proteus, for example *Pr. vulgaris, Pr. morganii, Pr. rettgeri, Pr. mirabilis* (Pr.=Proteus); Pseudomonadaceae, such as Pseudomonas bacteria, for example *Ps. aeruginosa* (Ps.=Pseudomonas); Bacteroidaceae, such as Bacteroides bacteria, for example *Bacteroides fragilis*; Mycoplasma, for example *Mycoplasma pneumonia*; also Mycobacteria, for example *Mycobacterium tuberculosis, Mycobacterium leprae* and atypical Mycobacteria.

The above list of pathogens is purely illustrative and is in no way to be interpreted as restrictive.

The following may be mentioned as examples of illnesses which can be prevented, ameliorated and/or healed by the compounds according to the invention: otitis; pharyngitis; pneumonia; peritonitis; pyelonephritis; cystitis; endocarditis; systemic infections; bronchitis; arthritis; local infections and septic illnesses.

The present invention includes pharmaceutical preparations which, in addition to non-toxic, inert pharmaceutically suitable vehicles, contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, pills, suppositories and ampules, of which the content of active compound corresponds to a function or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable vehicles there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary vehicles, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrants, for example agar-agar, calcium carbonate and sodium bicarbonate, (e) solution retarders, for example paraffin and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a microencapsulated form.

Suppositories can contain, in addition to the active compound or compounds, the customary water-soluble or water-insoluble vehicles, for example polyethylene glycols, fats, for example cacao fat, and higher esters (for example $C_{14}$-alcohol with $C_{16}$-fatty acid) or mixtures of these substances.

Ointments, pastes, creams and gels can contain the customary vehicles in addition to the active compound or compounds, for example animal and vegetable fats, waxes, paraffins, starch, tragacanth cellulose derivatives, polyethylene glycols, silicones, bentonites, silica, talc and zinc oxide or mixtures of these substances.

Powders and sprays can contain the customary vehicles, in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary vehicles in addition to the active compound or compounds such as solvents, solublizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, castor oil and sesame oil, lycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary vehicles in addition to the active compound or compounds, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colorants, preservatives and additives which improve the odor and flavor, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the compounds according to the invention.

The abovementioned pharmaceutical preparations are produced in the usual manner according to known methods, for example by mixing the active compound or compounds with the vehicle or vehicles.

The active compounds or the pharmaceutical preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds in total amounts of about 0.5 to about 500, preferably 1 to 50, mg/kg of body weight every 24 hours, optionally in the form of several individual administrations, in order to achieve the desired results. An individual administration contains the active compound or compounds preferably in amounts of about 0.5 to about 250, in particular 1 to 60, mg/kg of body weight. However, it can be necessary to deviate from the dosages mentioned and in particular to do so as a function of the nature and body weight of the subject to be treated, the nature and severity of the illness, the nature of the preparation and of the administration of the medicine, and the time or interval over which administration takes place.

Thus, it can suffice in some cases to manage with less than the abovementioned amount of active compound, whilst in other cases the abovementioned amount of active compound must be exceeded. The particular required optimum dosage and the type of administration of the active compounds can easily be decided by anyone skilled in the art on the basis of his expert knowledge.

The new compounds can be administered in the customary concentrations and preparations together with the feed or with feed preparations or with the drinking water. By this means, it is possible to prevent, ameliorate and/or heal an infection by Gram-negative or Gram-positive bacteria, and by this means to achieve promotion of growth and improvement in the utilization of the feed.

The compounds according to the invention are likewise suitable for the prevention and treatment of bacterial infection in fish.

It has already been disclosed in J. Med. Chem. 23, 1358 (1980) that 1-ethyl-6-fluoro-1,4-dihydro-4-oxo-7-(1-piperazinyl)-3-quinolinecarboxylic acid (norfloxacin) has antibacterial properties. However, the compounds according to the invention are superior to norfloxacin, as is evident from the table below, which indicates the MIC values of some of the compounds according to the invention and that of norfloxacin.

TABLE

| | MIC values (agar dilution test/isosensitest agar) | | | | | | | | | |
|---|---|---|---|---|---|---|---|---|---|---|
| | Example | | | | | | | | | |
| Strain | 1 | 2 | 3 | 5 | 8 | 11 | 12 | 14 | 16 | Norfloxacin |
| E. coli Neumann | 0.015 | 0.015 | 0.03 | 0.03 | ./. | ./. | 0.015 | 0.015 | 0.015 | 0.125 |
| Klebsiella 8085 | 0.015 | 0.015 | 0.03 | 0.03 | ./. | ./. | 0.015 | 0.03 | 0.015 | 0.25 |
| Klebsiella 6179 | 0.015 | 0.06 | 0.125 | 0.125 | ./. | ./. | 0.125 | 0.25 | 0.015 | 1 |
| Klebsiella 57 USA | 0.06 | 0.25 | 0.5 | 0.5 | ./. | ./. | 0.5 | 0.125 | 0.125 | 1 |
| Providencia 12052 | 4 | 8 | 8 | 8 | ./. | ./. | 8 | 32 | 4 | 0128 |
| Serratia 16040 | 8 | 16 | 16 | 16 | ./. | ./. | 16 | 8 | 2 | 32 |
| Staphylococcus FK 422 | 0.015 | 0.03 | 0.06 | 0.06 | 0.015 | 0.125 | 0.06 | 0.125 | 0.015 | 2 |
| Staphylococcus 1756 | 0.015 | 0.03 | 0.06 | 0.03 | 0.015 | 0.06 | 0.03 | 0.5 | 0.015 | 1 |
| Staphylococcus 133 | 0.015 | 0.06 | 0.06 | 0.06 | 0.03 | 0.06 | 0.03 | 0.125 | 0.015 | 1 |

PREPARATION EXAMPLES

Preparation of the starting materials (II)

Example A

1-Cyclopropyl-6,7,8-trifluoro-1,4-dihydro-4-oxo-3-quinolinecarboxylic acid

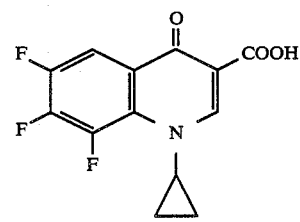

24.3 g of magnesium turnings are suspended in 50 ml of anhydrous ethanol. 5 ml of carbon tetrachloride are added and, when the reaction has started, a mixture of 160 g of diethyl malonate, 100 ml of absolute ethanol and 400 ml of anhydrous toluene are added dropwise at 50°-60° C. The mixture is then heated at 50°-60° C. for a further 1 hour, cooled with dry ice/acetone to −5° C. to −10° C. and a solution of 212.5 g of 2,3,4,5-tetrafluorobenzoyl chloride in 80 ml of absolute toluene is slowly added dropwise at this temperature. The mixture is stirred at 0° to −5° C. for 1 hour, allowed to reach room temperature overnight, and is then run into a mixture of 400 ml of ice-water and 25 ml of concentrated sulphuric acid while cooling in ice. The phases are separated and two further extractions with toluene are carried out. The combined toluene solutions are washed with saturated NaCl solution, dried with Na$_2$SO$_4$, and the solvent is removed in vacuo. 335 g of diethyl 2,3,4,5-tetrafluorobenzoylmalonate are obtained as a crude product.

0.3 g of p-toluenesulphonic acid is added to an emulsion of 284.8 g of crude diethyl 2,3,4,5-tetrafluorobenzoylmalonate in 300 ml of water. This mixture is heated to boiling, stirring vigorously for 5 hours, the cooled emulsion is extracted several times with methylene chloride, the combined methylene chloride solutions are washed once with saturated NaCl solution, dried with Na$_2$SO$_4$ and the solvent is removed by distillation in vacuo. Fractionation of the residue under high vacuum provides 160.2 g of ethyl 2,3,4,5-tetrafluorobenzoylacetate of boiling point 100°–110° C./0.09–0.1 mbar. Melting point 47°–49° C.

A mixture of 110.7 g of ethyl 2,3,4,5-tetrafluorobenzoyl acetate, 93.5 g of ethyl orthoformate and 107 g of acetic anhydride is heated at 150° C. for 2 hours. The volatile constituents are then removed by distillation under water pump vacuum and finally under high vacuum at a bath temperature of ~120° C. 123.9 g of crude ethyl 2-(2,3,4,5-tetrafluorobenzoyl)-3-ethoxyacrylate remain. This is sufficiently pure for the subsequent reactions.

23.2 g of cyclopropylamine are added dropwise, with stirring and cooling in ice, to a solution of 123.9 g of ethyl 2-(2,3,4,5-tetrafluorobenzoyl)-3-ethoxyacrylate in 250 ml of ethanol. When the exothermic reaction has subsided, the mixture is stirred for a further 1 hour at room temperature, the solvent is removed in vacuo, and the residue is recrystallized from cyclohexane/petroleum ether. 115 g of ethyl 2-(2,3,4,5-tetrafluorobenzoyl)-3-cyclopropylaminoacrylate of melting point 63°–65° C. are obtained.

21.2 g of sodium fluoride are added to a solution of 107.8 g of ethyl 2-(2,3,4,5-tetrafluorobenzoyl)-3-cyclopropylaminoacrylate in 400 ml of anhydrous dimethylformamide. The reaction mixture is then stirred under reflux for 2 hours and poured hot onto ice. The precipitate is filtered off with suction, thoroughly washed with water, and dried over calcium chloride at 100° C. in vacuo. 91.2 g of ethyl 1-cyclopropyl-6,7,8-trifluoro-1,4-dihydro-4-oxo-3-quinolinecarboxylate of melting point 167°–168° C. are obtained.

A mixture of 94 g of ethyl 1-cyclopropyl-6,7,8-trifluoro-1,4-dihydro-4-oxo-3-quinolinecarboxylate, 600 ml of glacial acetic acid, 450 ml of water and 70 ml of concentrated sulphuric acid is heated to reflux for 1.5 hours. The hot suspension is then poured onto ice, and the precipitate is filtered off with suction, thoroughly washed with water, and dried in vacuo at 100° C. In this manner, 88.9 g of pure 1-cyclopropyl-6,7,8-trifluoro-1,4-dihydro-4-oxo-3-quinolinecarboxylic acid II ($X^1=X^2=F$) of melting point 228°–230° C. (decomposition) are obtained.

Example B

1-Cyclopropyl-6,7-difluoro-1,4-dihydro-4-oxo-3-quinolinecarboxylic acid

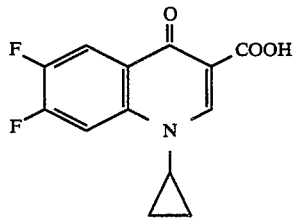

The process is carried out in analogy to Example A, starting from 2,4,5-trifluorobenzoyl fluoride and passing through the following stages: diethyl 2,4,5-trifluorobenzoylacetate (boiling point: 92°–95°/0.5 mbar; melting point: 53°–55°)→ethyl 2-(2,4,5-trifluorobenzoyl)-3-ethoxyacrylate (oil)→ethyl 2-(2,4,5-trifluorobenzoyl)-3-cyclopropylaminoacrylate (oil)→ethyl 1-cyclopropyl-6,7-difluoro-1,4-dihydro-4-oxo-3-quinolinecarboxylate (melting point 230°–233°)→1-cyclopropyl-6,7-difluoro-1,4-dihydro-4-oxo-3-quinolinecarboxylic acid (melting point: 302°–303° with decomposition).

Preparation of the active compounds (I)

Example 1

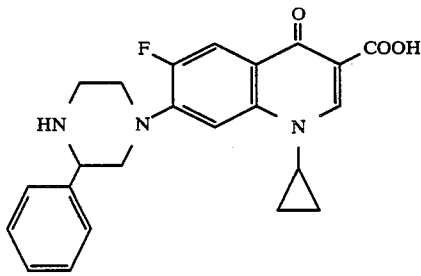

A mixture of 2.8 g (0.01 mols) of 7-chloro-1-cyclopropyl-6-fluoro-1,4-dihydro-4-oxo-3-quinolinecarboxylic acid, 1.8 g (0.011 mole) of 2-phenylpiperazine and 2.2 g (0.02 mole) of 1,4-diazabicyclo[2.2.2]octane in 6 ml of dimethyl sulphoxide is heated at 140° C. for 4 hours. The solution is concentrated under high vacuum, and the residue is stirred with 20 ml of water and the pH is adjusted to 7 with 2N hydrochloric acid. The precipitate is filtered off with suction, washed with water and methanol, and boiled in 30 ml of methanol. 1.3 g (32% of theory) of 1-cyclopropyl-6-fluoro-1,4-dihydro-4-oxo-7-(3-phenyl-1-piperazinyl)-3-quinolinecarboxylic acid of melting point 218°–220° (with decomposition) is obtained (recrystallized from glycol monomethyl ether).

The same product is obtained when 1-cyclopropyl-6,7-difluoro-1,4-dihydro-4-oxo-3-quinolinecarboxylic acid is reacted correspondingly with 2-phenylpiperazine.

The following compounds are obtained in analogy to Example 1 using the appropriate piperazines:

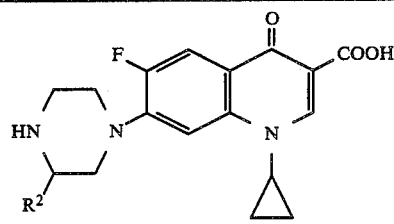

| Example | R² | Melting point (with decomposition) |
|---|---|---|
| 2 | F—⟨phenyl⟩— | 198–203° |
| 3 | Cl—⟨phenyl⟩— | 207–209° (from methanol) |
| 4 | Br—⟨phenyl⟩— | 252–255° |
| 5 | CH₃O—⟨phenyl⟩— | 208–211° (from ethanol) |
| 6 | ⟨phenyl⟩—CH₂—O—⟨phenyl⟩— | 208–211° (from methanol) |
| 7 | 3,4,5-tri(CH₃O/CH₃)—⟨phenyl⟩— | 233–237° (from glycol monomethyl ether) |
| 8 | ⟨piperidinyl⟩—N—⟨phenyl⟩— | 156–161° |
| 9 | H₃C—⟨phenyl⟩— | 258–261° |
| 10 | ⟨biphenyl⟩— | 278–281° |
| 11 | NO₂—⟨phenyl⟩— | 247–250° (from methanol) |

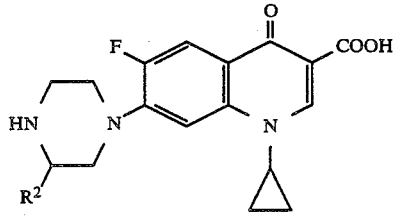

| Example | R² | Melting point (with decomposition) |
|---|---|---|
| 12 | ⟨thienyl⟩— | 218–222° (from acetonitrile) |
| 13 | ⟨cyclohexyl⟩— .HCl | 316–320° (from methanol) |

Example 14

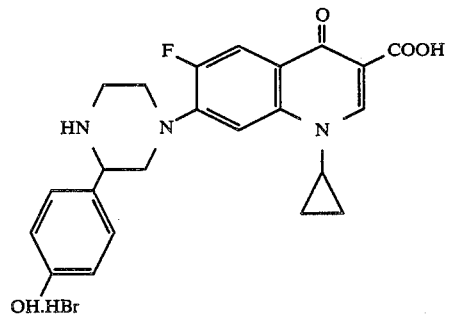

60 ml of 48% strength hydrobromic acid are added to 2,5 g (4.9 mmoles) of the product from Example 6 in 30 ml of ethanol, and the mixture is stirred at 55° for 1 hour. It is concentrated in vacuo, the residue is stirred with 50 ml of water, and the precipitate is filtered off with suction and washed with methanol. 1.5 g (66% of theory) of 1-cyclopropyl-6-fluoro-1,4-dihydro-7-[3-(4-hydroxyphenyl)-1-piperazinyl]-4-oxo-3-quinolinecarboxylic acid hydrobromide of melting point 295°–298° (with decomposition) is obtained.

Example 15

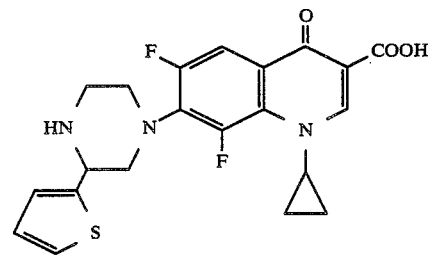

2.8 g (0.01 mole) of 1-cyclopropyl-6,7,8-trifluoro-1,4-dihydro-4-oxo-3-quinolinecarboxylic acid (Example A) are heated to 140° C. together with 1.8 g (0.011 mole) of 2-(2-thienyl)piperazine and 2.2 g (0.02 mole) of 1,4- diazobicyclo[2.2.2]octane in 6 ml of DMSO for 2 hours. The mixture is concentrated under high vacuum, the residue is stirred with 20 ml of water, and the precipitate is filtered off with suction and boiled in 20 ml of methanol. 2.4 g (56% of theory) of 1-cyclopropyl-6,8-difluoro-1,4-dihydro-4-oxo-7-[3-(2-thienyl)-1-piperazinyl]-3-quinolinecarboxylic acid of melting point 252°–254° C. (with decomposition) are obtained. The melting point remains unchanged after recrystallization from glycol monomethyl ether.

The following compounds are obtained in analogy to Example 15:

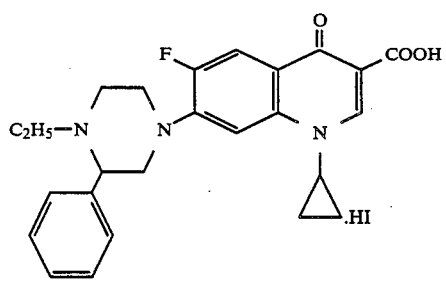

| Example | R² | Melting point (with decomposition) |
|---|---|---|
| 16 | phenyl | 245–247° |
| 17 | 4-fluorophenyl | 244–245° |
| 18 | bromophenyl | 242–245° |

Example 19

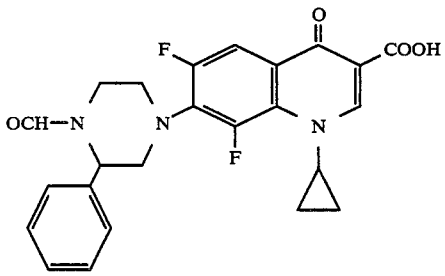

1.1 g (2.7 mmoles) of the product from Example 1 in 10 ml of dimethyl formamide are heated at 80° with 0.6 g of triethylamine and 0,9 g of ethyl iodide for 3 hours. The reaction mixture is concentrated in vacuo, and the residue is stirred with 10 ml of water and recrystallized from glycol monomethyl ether. 0.75 g (49% of theory) of 1-cyclopropyl-7-4-ethyl-3-phenyl-1-piperazinyl-6-fluoro-1,4-dihydro-4-oxo-3-quinolinecarboxylic acid hydroiodide of melting point 240°–243° (with decomposition) is obtained.

Example 20

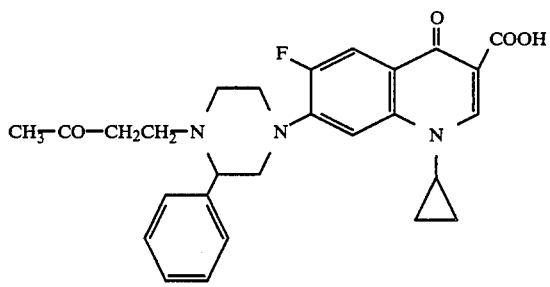

1.1 g (2.7 mmoles) of the product from Example 1 in 15 ml of ethanol is heated under reflux with 1.05 g of methyl vinyl ketone for 8 hours. The precipitate is filtered off with suction and washed with ethanol. 0.9 g (70% of theory) of 1-cyclopropyl-6-fluoro-1,4-dihydro-4-oxo-7-[4-(3-oxobutyl)-3-phenyl-1-piperazinyl]-3-quinolinecarboxylic acid of melting point 224°–226° (with decomposition) is obtained.

Example 21

0.8 g (1.9 mmoles) of the compound from Example 16 in 6 ml of dimethylformamide are heated under reflux with 0.6 ml of 98–100% strength formic acid for 8 hours. The reaction mixture is concentrated in vacuo, and the residue is stirred with 20 ml of water and the pH is adjusted to 5 with 5% strength sodium bicarbonate solution. The precipitate which has separated out is filtered off with suction, washed with water and methanol and recrystallized from glycol monomethyl ether. 0.6 g (70% of theory) of 1-cyclopropyl-6,8-difluoro-7-(4-formyl-3-phenyl-1-piperazinyl)-1,4-dihydro-4-oxo-3-quinolinecarboxylic acid of melting point 242°–245° (with decomposition) is obtained.

| Example for a tablet according to the invention | |
|---|---|
| Each tablet contains: | |
| Compound of the example | 291.5 mg |
| Microcrystalline cellulose | 27.5 mg |
| Corn starch | 36.0 mg |
| Poly(1-vinyl-2-pyrrolidone) insoluble | 15.0 mg |
| Highly disperse silica | 2.5 mg |
| Magnesium stearate | 2.5 mg |
| | 375.0 mg |
| The Lacquer coating contains: | |
| Poly(O—hydroxypropyl-O—methyl)cellulose 15 cp (hydroxypropylmethylcellulose USP) | 3.9 mg |
| Macrogol 4000 rec. INN (polyethylene glycols DAB) | 1.3 mg |
| Titanium (IV) oxide (titanium dioxide BP) | 1.3 mg |
| | 6.5 mg |

It will be understood that the specification and examples are illustrative but not limitative of the present invention and that other embodiments within the spirit and scope of the invention will suggest themselves to those skilled in the art.

We claim:

1. A 1-cyclopropyl-6-fluoro-1,4-dihydro-4-oxo-7-(1-piperazinyl)-3-quinolinecarboxylic acid of the formula

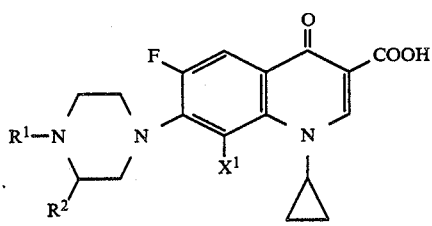

in which
R¹ is hydrogen, alkyl with 1 to 4 carbon atoms and optionally substituted by hydroxyl, methoxy, amino, dimethylamino, halogen, cyano or alkoxycarbonyl having 1 or 2 carbon atoms in the alkyl moiety, or is oxoalkyl having up to 4 carbon atoms, phenacyl, or acyl having 1 to 4 carbon atoms, R² is phenyl or cyclohexyl optionally substituted up to three times by halogen, methyl, phenyl, cyano, hydroxyl, methoxy, benzyloxy, amino, methylamino, dimethylamino, piperidino or nitro, or is methylenedioxyphenyl, methylenedioxycyclohexyl, furyl, tetrahydrofuryl or thienyl, and X¹ is hydrogen or fluorine, or a pharmaceutically utilizable hydrate, acid addition salt, alkali metal or alkaline earth metal salt thereof.

2. A 1-cyclopropyl-6-fluoro-1,4-dihydro-4-oxo-7-(1-piperazinyl)-3-quinolinecarboxylic acid, hydrate or salt according to claim 1, in which
R¹ is hydrogen, alkyl with 1 to 4 carbon atoms and optionally substituted by hydroxyl, methoxy, halogen, cyano or alkoxycarbonyl having 1 or 2 carbon atoms in the alkyl moiety, or is oxoalkyl having up to 4 carbon atoms, phenacyl, formyl or acetyl, and R² is phenyl or cyclohexyl optionally substituted up to three times by chlorine, bromine, fluorine, methyl, phenyl, cyano, hydroxyl, methoxy, benzyloxy, amino, piperidino or nitro, or is thienyl.

3. A 1-cyclopropyl-6-fluoro-1,4-dihydro-4-oxo-7-(1-piperazinyl)-3-quinolinecarboxylic acid, hydrate or salt according to claim 1,
in which
R¹ is hydrogen, alkyl with 1 to 3 carbon atoms and optionally substituted by hydroxyl, methoxy, cyano or alkoxy carbonyl having 1 or 2 carbon atoms in the alkyl moiety, or is oxoalkyl having up to 4 carbon atoms, phenacyl, formyl or acetyl, R² is phenyl or cyclohexyl optionally substituted up to three times by chlorine, bromine, fluorine, methyl, phenyl, hydroxyl, methoxy, benzyloxy, amino, piperidino or nitro, or is thienyl.

4. A compound according to claim 1, wherein such compound is 1-cyclopropyl-6-fluoro-1,4-dihydro-4-oxo-7-(3-phenyl-1-piperazinyl)-3-quinolinecarboxylic acid of the formula

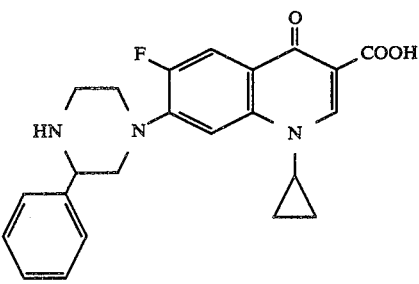

or a pharmaceutically utilizable hydrate, acid addition salt, alkali metal or alkaline earth metal salt thereof.

5. A compound according to claim 1, wherein such compound is 1-cyclopropyl-6-fluoro-1,4-dihydro-4-oxo-7-[3-(4-fluorophenyl)-1-piperazinyl]-3-quinolinecarboxylic acid of the formula

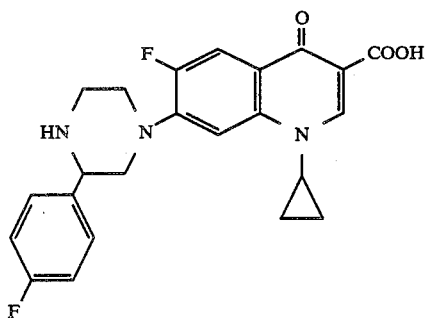

or a pharmaceutically utilizable hydrate, acid addition salt, alkali metal or alkaline earth metal salt thereof.

6. A compound according to claim 1, wherein such compound is 1-cyclopropyl-6-fluoro-1,4-dihydro-4-oxo-7-{3-[4-(1-piperidinyl)-phenyl]-1-piperazinyl}-3-quinolinecarboxylic acid of the formula

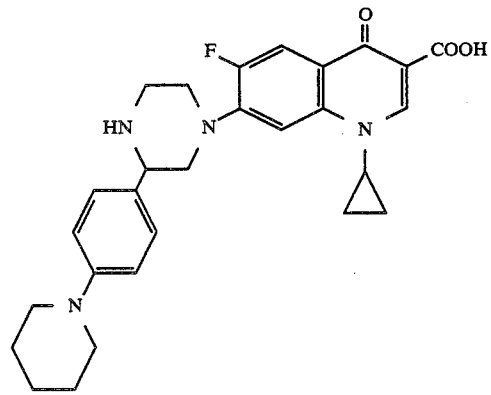

or a pharmaceutically utilizable hydrate, acid addition salt, alkali metal or alkaline earth metal salt thereof.

7. A compound according to claim 1, wherein such compound is 1-cyclopropyl-6,8-difluoro-1,4-dihydro-4-oxo-7-[3-(2-thienyl)-1-piperazinyl]-3-quinolinecarboxylic acid of the formula

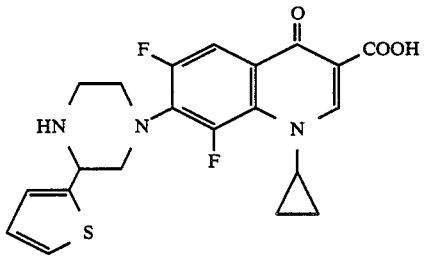

or a pharmaceutically utilizable hydrate, acid addition salt, alkali metal or alkaline earth metal salt thereof.

8. A compound according to claim 1, wherein such compound is 1-cyclopropyl-6,8-difluoro-1,4-dihydro-4-oxo-7-(3-phenyl-1-piperazinyl)-3-quinolinecarboxylic acid of the formula

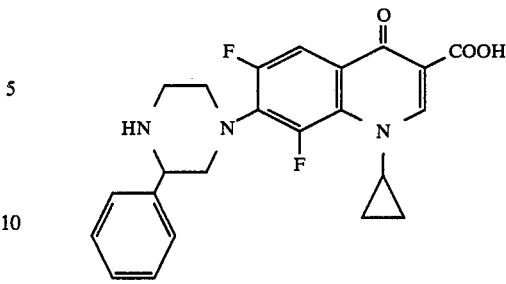

or a pharmaceutically utilizable hydrate, acid addition salt, alkali metal or alkaline earth metal salt thereof.

9. An antibacterial composition comprising an antibacterially effective amount of a compound, hydrate or salt according to claim 1 in admixture with a diluent.

10. A unit dose of a composition according to claim 9 in the form of a tablet, capsule or ampule.

11. A method of combating bacteria which comprises applying to such bacteria or to a host from which it is desired to exclude such bacteria an antibacterially effective amount of a compound, hydrate or salt according to claim 1.

12. The method according to claim 11, wherein such compound is
1-cyclopropyl-6-fluoro-1,4-dihydro-4-oxo-7-(3-phenyl-1-piperazinyl)-3-quinolinecarboxylic acid,
1-cyclopropyl-6-fluoro-1,4-dihydro-4-oxo-7-[3-(4-fluorophenyl)-1-piperazinyl]-3-quinolinecarboxylic acid,
1-cyclopropyl-6-fluoro-1,4-dihydro-4-oxo-7-{3-[4-1-piperidinyl)-phenyl]-1-piperazinyl}-3-quinolinecarboxylic acid,
1-cyclopropyl-6,8-difluoro-1,4-dihydro-4-oxo-7-[3-(2-thienyl)-1-piperazinyl]-3-quinolinecarboxylic acid or
1-cyclopropyl-6,8-difluoro-1,4-dihydro-4-oxo-7-(3-phenyl-1-piperazinyl)-3-quinolinecarboxylic acid,
or a pharmaceutically utilizable hydrate, acid addition salt, alkali metal or alkaline earth metal salt thereof.

* * * * *